(12) United States Patent
Kimchy et al.

(10) Patent No.: US 9,895,116 B2
(45) Date of Patent: Feb. 20, 2018

(54) LINEAR FAIL SAFE RADIATION CONCEALMENT MECHANISM

(71) Applicant: CHECK-CAP LTD., Isfiya (IL)

(72) Inventors: Yoav Kimchy, Haifa (IL); Shai Brenner, Haifa (IL)

(73) Assignee: CHECK-CAP LTD., Isfiya (IL)

( * ) Notice: Subject to any disclaimer, the term of this patent is extended or adjusted under 35 U.S.C. 154(b) by 120 days.

(21) Appl. No.: 15/025,895

(22) PCT Filed: Nov. 18, 2014

(86) PCT No.: PCT/IL2014/050998
§ 371 (c)(1),
(2) Date: Mar. 30, 2016

(87) PCT Pub. No.: WO2015/075711
PCT Pub. Date: May 28, 2015

(65) Prior Publication Data
US 2016/0228077 A1 Aug. 11, 2016

Related U.S. Application Data

(60) Provisional application No. 61/908,184, filed on Nov. 25, 2013.

(51) Int. Cl.
*G01V 5/08* (2006.01)
*G21K 1/02* (2006.01)
(Continued)

(52) U.S. Cl.
CPC ............ *A61B 6/4057* (2013.01); *A61B 1/041* (2013.01); *A61B 5/065* (2013.01); *A61B 6/06* (2013.01); *A61B 6/107* (2013.01); *A61B 6/425* (2013.01); *A61B 6/4258* (2013.01); *A61B 6/4476* (2013.01); *A61B 6/481* (2013.01); *A61B 6/482* (2013.01); *A61B 6/483* (2013.01); *A61B 6/485* (2013.01); *A61B 6/54* (2013.01);
(Continued)

(58) Field of Classification Search
CPC ....... A61B 6/4057; A61B 6/54; A61B 6/4405; A61B 2090/376; A61B 5/004; A61B 5/02755; A61B 5/0538; A61B 5/4238; A61B 1/05; A61B 1/041; A61B 5/0084; A61B 1/273; A61B 2562/162; G01V 5/08; G01V 5/12; G01V 5/125; G01V 5/04
USPC .................... 378/91, 147; 600/436, 109, 118
See application file for complete search history.

(56) References Cited

U.S. PATENT DOCUMENTS

2007/0161885 A1 7/2007 Kimchy et al.
2012/0045127 A1 2/2012 Song et al.
(Continued)

FOREIGN PATENT DOCUMENTS

WO 2012/123093 9/2012

*Primary Examiner* — Don Wong
(74) *Attorney, Agent, or Firm* — Soroker Agmon Nordman

(57) ABSTRACT

A fail safe concealment mechanism for a radiation imaging capsule, including, a collimator having a first area that blocks radiation and an second area that releases radiation, a radiation source that is initially positioned inside the collimator in the area that blocks radiation, a linear mechanism that moves the radiation source inside the collimator to the area that releases radiation when power is provided to the mechanism and automatically returns the radiation source to the area that blocks radiation when power is not provided to the mechanism.

18 Claims, 7 Drawing Sheets

(51) Int. Cl.
*A61B 6/00* (2006.01)
*A61B 6/10* (2006.01)
*A61B 6/06* (2006.01)
*A61B 1/04* (2006.01)
*A61B 5/06* (2006.01)

(52) U.S. Cl.
CPC .............. *A61B 6/542* (2013.01); *A61B 6/547* (2013.01); *A61B 6/56* (2013.01); *A61B 2562/162* (2013.01)

(56) References Cited

U.S. PATENT DOCUMENTS

2013/0172740 A1    7/2013  Kimchy et al.
2014/0037069 A1*   2/2014  Kimchy ............... A61B 6/4057
                                                378/147

* cited by examiner

FIG. 7

```
┌─────────────────────────────────────┐
│ INSTALL A COLLIMATOR HAVING A FIRST AREA │
│ THAT BLOCKS RADIATION AND A SECOND AREA  │──710
│      THAT RELEASES RADIATION              │
└─────────────────────────────────────┘
                  ↓
┌─────────────────────────────────────┐
│ POSITION THE RADIATION SOURCE INSIDE THE │
│ FIRST AREA OF THE COLLIMATOR, SO THAT    │──720
│       THE RADIATION IS BLOCKED            │
└─────────────────────────────────────┘
                  ↓
┌─────────────────────────────────────┐
│ DEPLOY A LINEAR MECHANISM THAT MOVES      │
│ THE RADIATION SOURCE TO THE SECOND AREA   │
│ WHEN POWER IS PROVIDED TO THE MECHANISM   │──730
│ AND RETURNS THE RADIATION SOURCE TO BE    │
│ BLOCKED BY THE FIRST AREA OF THE          │
│ COLLIMATOR WHEN POWER IS UNAVAILABLE      │
└─────────────────────────────────────┘
```

LINEAR FAIL SAFE RADIATION CONCEALMENT MECHANISM

RELATED APPLICATIONS

This application claims priority under 35 U.S.C. 120 from U.S. provisional application No. 61/908,184 dated Nov. 25, 2013, the disclosure of which is incorporated herein by reference.

FIELD OF THE DISCLOSURE

The present disclosure relates generally to limiting exposure of a patient to radiation and more specifically to a fail-safe radiation concealment mechanism in an imaging capsule that is swallowed by a patient to examine the patients gastrointestinal tract.

BACKGROUND OF THE DISCLOSURE

One method for examining the gastrointestinal tract for the existence of polyps and other clinically relevant features that may indicate regarding the potential of cancer is performed by swallowing an imaging capsule that travels through the gastrointestinal tract and view the patients situation. In a typical case the trip can take between 24-48 hours after, which the imaging capsule exits in the patients feces. Typically the patient swallows a contrast agent to enhance the imaging ability of the imaging capsule. Then the patient swallows the imaging capsule to examine the gastrointestinal tract while flowing through the contrast agent. The imaging capsule typically includes a radiation source, for example including a radioisotope that emits X-rays and/or Gamma rays. The radiation is typically collimated to allow it to be controllably directed toward a specific area during the imaging process. In an exemplary case the imaging capsule is designed to measure X-Ray fluorescence and/or Compton back-scattering and transmit the measurements (e.g. count rate) to an external analysis device, for example a computer or other dedicated instruments.

U.S. Pat. No. 7,787,926 to Kimchy the disclosure of which is incorporated herein by reference, describes details related to the manufacture and use of such an imaging capsule.

Use of an imaging capsule exposes the user to radiation, which may be potentially harmful. Accordingly, it is of interest to limit the user's exposure to radiation when not necessary, for example while the imaging capsule is located in positions that do not need to be measured. Typically, the imaging capsule may be designed with shutters that can be instructed to block the emission of radiation when not needed. However, there still exists the hazard that in case of malfunction of the imaging capsule, for example in case of a power failure the shutters may be stuck in the open position and radiation may be emitted without constraint.

It is thus desirable to design a fail-safe radiation blocking mechanism that automatically blocks the emission of radiation, only allowing radiation to be emitted if power is available and the device provides an instruction to allow radiation to be emitted.

Another consideration is power consumption. It is desirable to conserve energy and scan with the capsule only when movement of the capsule in the colon occurs, therefore, the concealment mechanism should be designed to use as little power as possible yet to enable activation and scanning by electrical control.

SUMMARY OF THE DISCLOSURE

An aspect of an embodiment of the disclosure, relates to an imaging capsule with a fail-safe radiation mechanism that prevents the emission of radiation from the imaging capsule until the imaging capsule is instructed to emit radiation and power is available to activate a linear actuator to move a radiation source linearly to unblock the emission of radiation. In contrast when power is not available the radiation source returns automatically to a position that renders radiation emission to be blocked. Optionally, when power is available the linear motion causes the imaging capsule to emit radiation scanning substantially an entire circumference surrounding the capsule (e.g. 360°) perpendicular to the linear motion. Alternatively, the user may select the radiation emission pattern.

In an exemplary embodiment of the disclosure, the linear actuator comprises a mechanism that uses a linear voice coil motor having a magnetic housing and a voice coil configured to move linearly back and forth. Alternatively, the linear actuator comprises a mechanism that uses a per anent magnet attached to the radiation source and a solenoid wrapped around a ferromagnetic core to form an electromagnet to selectively repel the radiation source to the area that releases radiation. Further alternatively, the linear actuator comprises a mechanism that uses a shape memory alloy spring that expands responsive to the transfer of electrical current through the material and retracts to a remembered shape when electrical current is not provided. Optionally, the mechanism also includes a spring to return the radiation source to the area that blocks radiation when power is not provided to the mechanism.

There is thus provided according to an exemplary embodiment of the disclosure, a fail safe concealment mechanism for a radiation imaging capsule, comprising:

A collimator having a first area that blocks radiation and a second area that releases radiation;

A radiation source that is initially positioned inside the collimator in the area that blocks radiation;

A linear mechanism that moves the radiation source inside the collimator to the area that releases radiation when power is provided to the mechanism and automatically returns the radiation source to the area that blocks radiation when power is not provided to the mechanism.

In an exemplary embodiment of the disclosure, the mechanism further comprises a control unit that controls the timing of the linear mechanism. Optionally, the control unit is programmed to provide power so that the motion frequency of the radiation source matches the natural resonance oscillatory frequency of the linear mechanism.

In an exemplary embodiment of the disclosure, the area that releases radiation in the collimator has a spiral slit that releases radiation in different directions as a function of the position of the radiation source inside the collimator. Optionally, as the radiation source moves linearly through the area that releases radiation in the collimator it emits a beam that scans 360° around the imaging capsule. In an exemplary embodiment of the disclosure, the linear mechanism comprises a linear voice coil motor having a magnetic housing and a voice coil that is configured to move linearly back and forth. Optionally, the linear mechanism comprises a spring to return the radiation source to the area that blocks radiation when power is not provided to the mechanism. In an exemplary embodiment of the disclosure, the linear mechanism comprises a permanent magnet attached to the radiation source and a solenoid wrapped around a ferromagnetic core to form an electromagnet to selectively repel the radiation source to the area that releases radiation. Optionally, the linear mechanism comprises a Hall Effect sensor or LDVT sensor to determine the position of the permanent magnet and enable a controller to control the motion of the radiation source in the collimator. In an exemplary embodiment of the disclosure, the linear mechanism comprises a shape memory alloy spring that expands responsive to the transfer of electrical current through the material and retracts to a remembered shape when electrical current is not provided.

There is further provided according to an exemplary embodiment of the disclosure, a method of equipping a radiation imaging capsule with a fail safe concealment mechanism, comprising:

Installing a collimator having a first area that blocks radiation and a second area that releases radiation;

Positioning a radiation source inside the collimator in the area that blocks radiation;

Deploying a linear mechanism that moves the radiation source inside the collimator to the area that releases radiation when power is provided to the mechanism and automatically returns the radiation source to the area that blocks radiation when power is not provided to the mechanism.

In an exemplary embodiment of the disclosure, a control unit controls the timing of the linear mechanism. Optionally, the control unit is programmed to provide power so that the motion frequency of the radiation source matches the natural resonance oscillatory frequency of the linear mechanism. In an exemplary embodiment of the disclosure, the area that releases radiation in the collimator has a spiral slit that releases radiation in different directions as a function of the position of the radiation source inside the collimator. Optionally, as the radiation source moves linearly through the area that releases radiation in the collimator it emits a beam that scans 360° around the imaging capsule. In an exemplary embodiment of the disclosure, the linear mechanism comprises a linear voice coil motor having a magnetic housing and a voice coil that is configured to move linearly back and forth. Optionally, the linear mechanism comprises a spring to return the radiation source to the area that blocks radiation when power is not provided to the mechanism. In an exemplary embodiment of the disclosure, the linear mechanism comprises a permanent magnet attached to the radiation source and a solenoid wrapped around a ferromagnetic core to form an electromagnet to selectively repel the radiation source to the area that releases radiation. Optionally, the linear mechanism comprises a Hall Effect sensor or LDVT sensor to determine the position of the permanent magnet and enable a controller to control the motion of the radiation source in the collimator. In an exemplary embodiment of the disclosure, the linear mechanism comprises a shape memory alloy spring that expands responsive to the transfer of electrical current through the material and retracts to a remembered shape when electrical current is not provided.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein:

FIG. 7 is a flow diagram of a method of blocking and unblocking the emission of radiation with a linear actuator, according to an exemplary embodiment of the disclosure.

DETAILED DESCRIPTION

In an exemplary embodiment of the disclosure, a patient swallows a contrast agent which mixes with the content of their gastrointestinal tract to increase the accuracy of the measurements. Then the patient swallows an imaging capsule to examine the gastrointestinal tract as the imaging capsule traverses the gastrointestinal tract. In an exemplary embodiment of the disclosure, the imaging capsule is designed to automatically block radiation from being emitted from it until receiving instructions to release radiation and sample its surroundings by emitting a radiation beam that sweeps through substantially 360° around a circumference of the imaging capsule. In an exemplary embodiment of the disclosure, power is required to prevent blocking the emission of radiation. Optionally, if the imaging capsule lacks power the radiation will be blocked.

Figure 1:
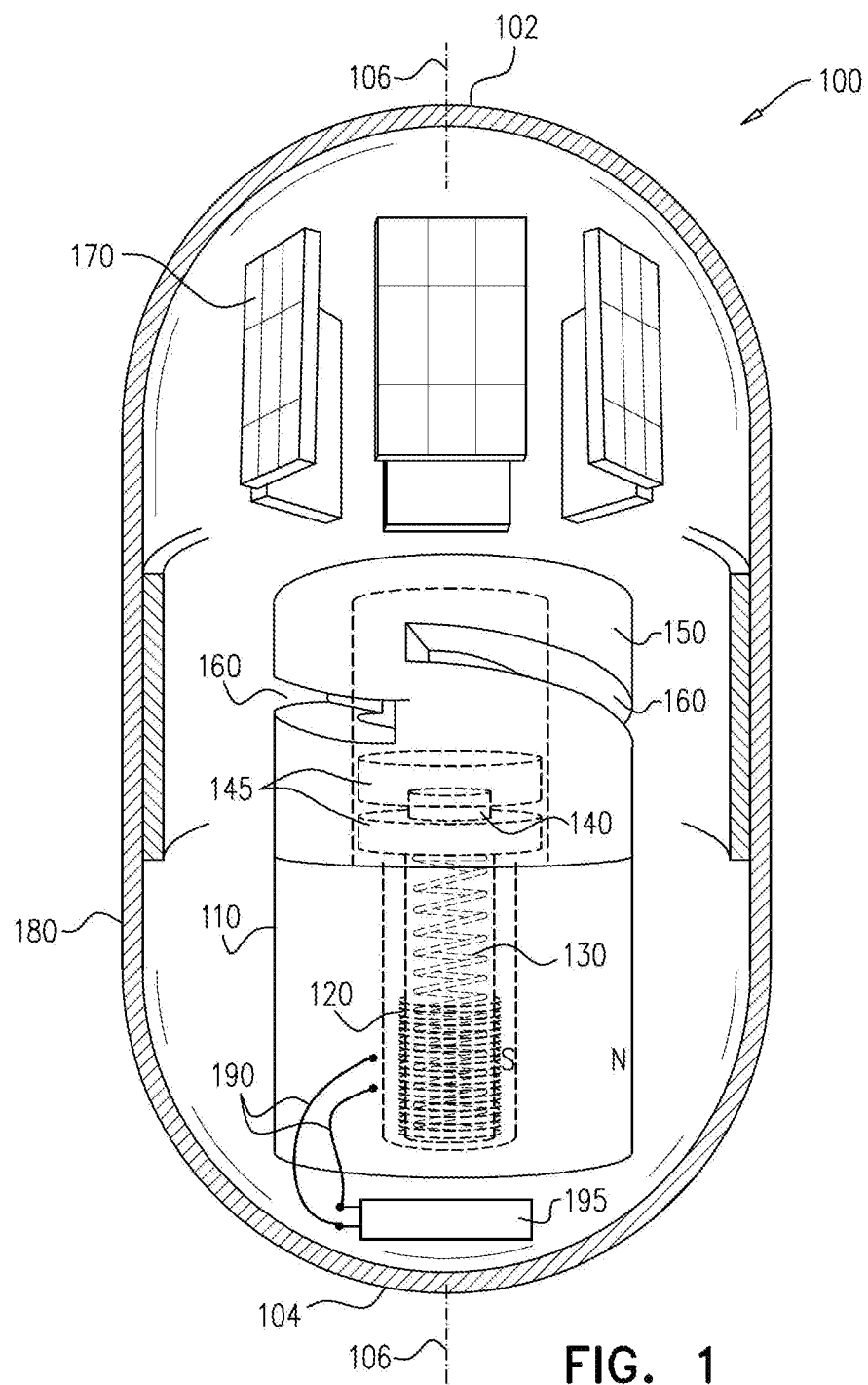
FIG. 1 is a schematic illustration of a cross sectional perspective view of a failsafe imaging capsule blocking radiation, according to an exemplary embodiment of the disclosure.
Figure 2:
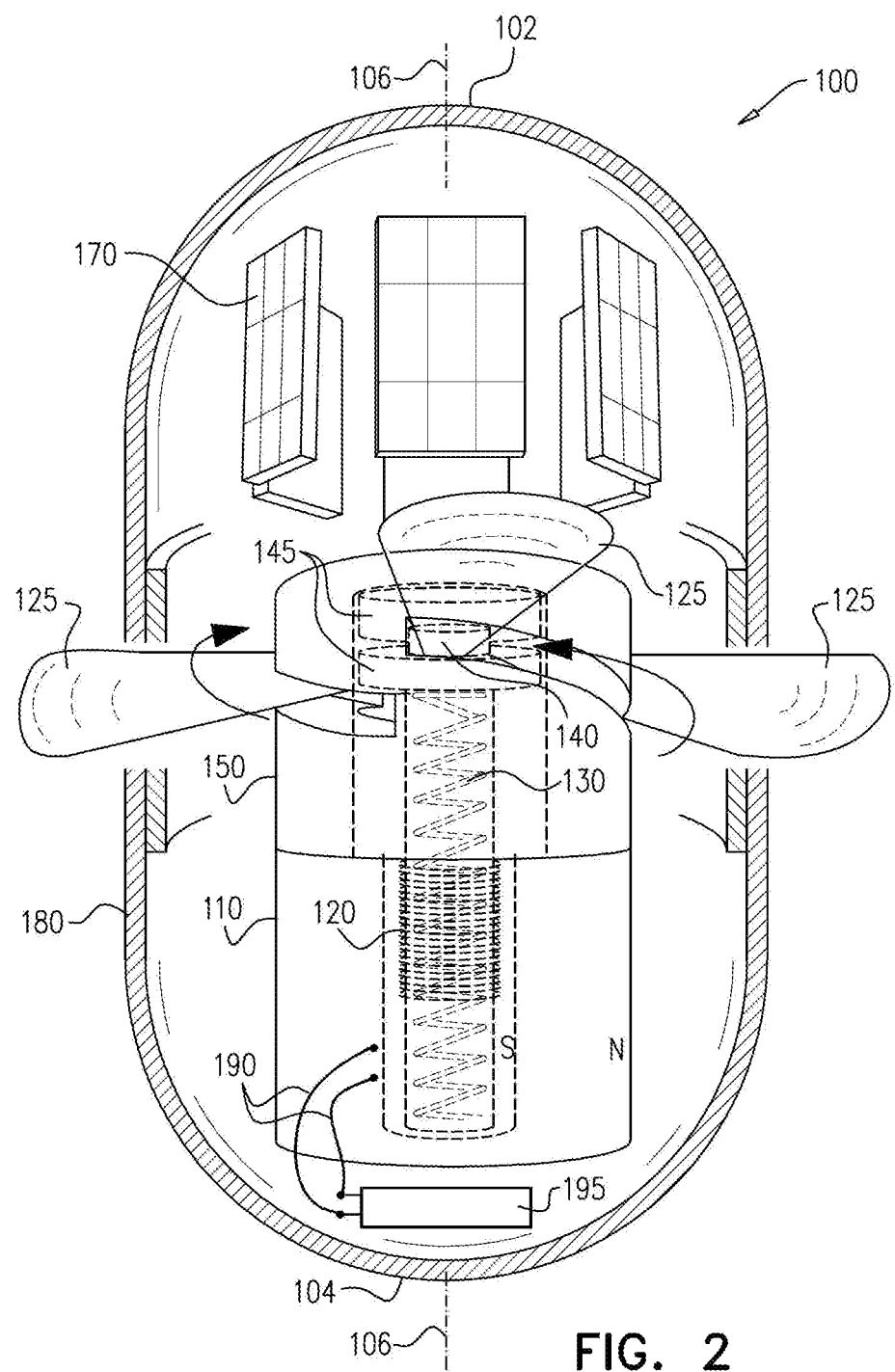
FIG. 2 is a schematic illustration of a cross sectional perspective view of a failsafe imaging capsule emitting radiation, according to an exemplary embodiment of the disclosure.

FIG. 1 is a schematic illustration of a cross sectional perspective view of a failsafe imaging capsule 100 blocking radiation, and FIG. 2 is a schematic illustration of a cross sectional perspective view of failsafe imaging capsule 100 emitting radiation, according to an exemplary embodiment of the disclosure.

Optionally, the imaging capsule 100 comprises an encasement 180 shaped as an elongated cylinder with an elongated axis 106 and having flat or spherically shaped ends, upper end 102 and lower end 104. Alternatively, other shapes may be used, for example a parallelepiped having flat ends, pyramid shaped ends or other shapes. In an exemplary embodiment of the disclosure, imaging capsule 100 includes a radiation source 140 that emits x-ray or gamma radiation and is positioned inside a collimator 150 (e.g. a cylindrical collimator) to control the emission of radiation from the radiation source 140. Optionally, the radiation source is also located between two radiation blocking disks 145 (e.g. cylindrical tungsten disks) to prevent emission of radiation from the upper end 102 and the lower end 104 of the imaging capsule 100. In an exemplary embodiment of the disclosure, the collimator includes a first area which completely blocks the emission of radiation and a second area with a spiral slit 160 that enables the emission of radiation in a different direction depending on the position of radiation source 140 along the elongated axis 106. Optionally, when radiation source 140 is moved linearly back and forth in the second area the radiation source 140 forms a radiation beam 125 through the spiral slits 160 that covers the entire circumference of imaging capsule 100. Optionally, radiation beam 125 is shaped as a quasi cone shaped radiation beam that rotates around the radiation source 140 in response to the linear motion of the radiation source 140.

In an exemplary embodiment of the disclosure, imaging capsule 100 includes detectors 170 that receive a signal in response to the radiation beam 125. The signal received by detectors 170 are provided to a control 195 for analysis. Optionally, control 195 includes a transceiver to wirelessly communicate and receive external instructions, for example to start or stop scanning and to transmit recorded information to an external computer for analysis. In an exemplary embodiment of the disclosure, a general purpose computer having a processor and memory serves as the external computer to receive the detected signals and construct an image of the gastrointestinal tract. Alternatively or additionally, a dedicated transmission device may be used to send instructions to the imaging capsule 100 and record information transmitted from imaging capsule 100.

In an exemplary embodiment of the disclosure, radiation source 140 is placed on a linear voice coil motor having a magnetic housing 110 and a voice coil 120. Optionally, the voice coil 120 is designed to move back and forth in a void inside magnetic housing 110 along the elongated axis 106. The motion of voice coil 120 moves radiation source 140 from the first area to the second area of collimator 150 so that imaging capsule 100 scans the gastrointestinal tract with radiation beam 125. Optionally, control 195 controls the provision of electrical current through current lines 190 to the voice coil 120 of the linear voice coil motor. In an exemplary embodiment of the disclosure, a spring 130 is connected to resist moving radiation source 140 to the second area and automatically return radiation source 140 to the first area of collimator 150, so that in the absence of electrical power the emission of radiation will be blocked. For example spring 130 may be physically connected between one of the blocking disks 145 to lower end 104 or to a base of magnetic housing 110.

In an exemplary embodiment of the disclosure, control 195 controls the duration and direction of emission of radiation by radiation source 140 based on the provision of power to voice coil 120. Optionally, control 195 may be designed to scan in a specific pattern or may be designed to conserve energy by taking advantage of the natural resonance oscillatory frequency of spring 130 and the moving masses. In an exemplary embodiment of the disclosure, controller 195 only contributes impulses at small intervals to compensate for friction loss while the radiation source 140 moves linearly back and forth to optimally image the gastrointestinal tract. In an exemplary embodiment of the disclosure, the natural resonance oscillatory frequency is calculated by:

$$f = \left(\frac{1}{2\pi}\right)\sqrt{\frac{K}{m}}$$

Where K is the spring constant [Newton/meter], m is the moving mass attached to the spring [Kg] and f is the resonance frequency.

Figure 3:
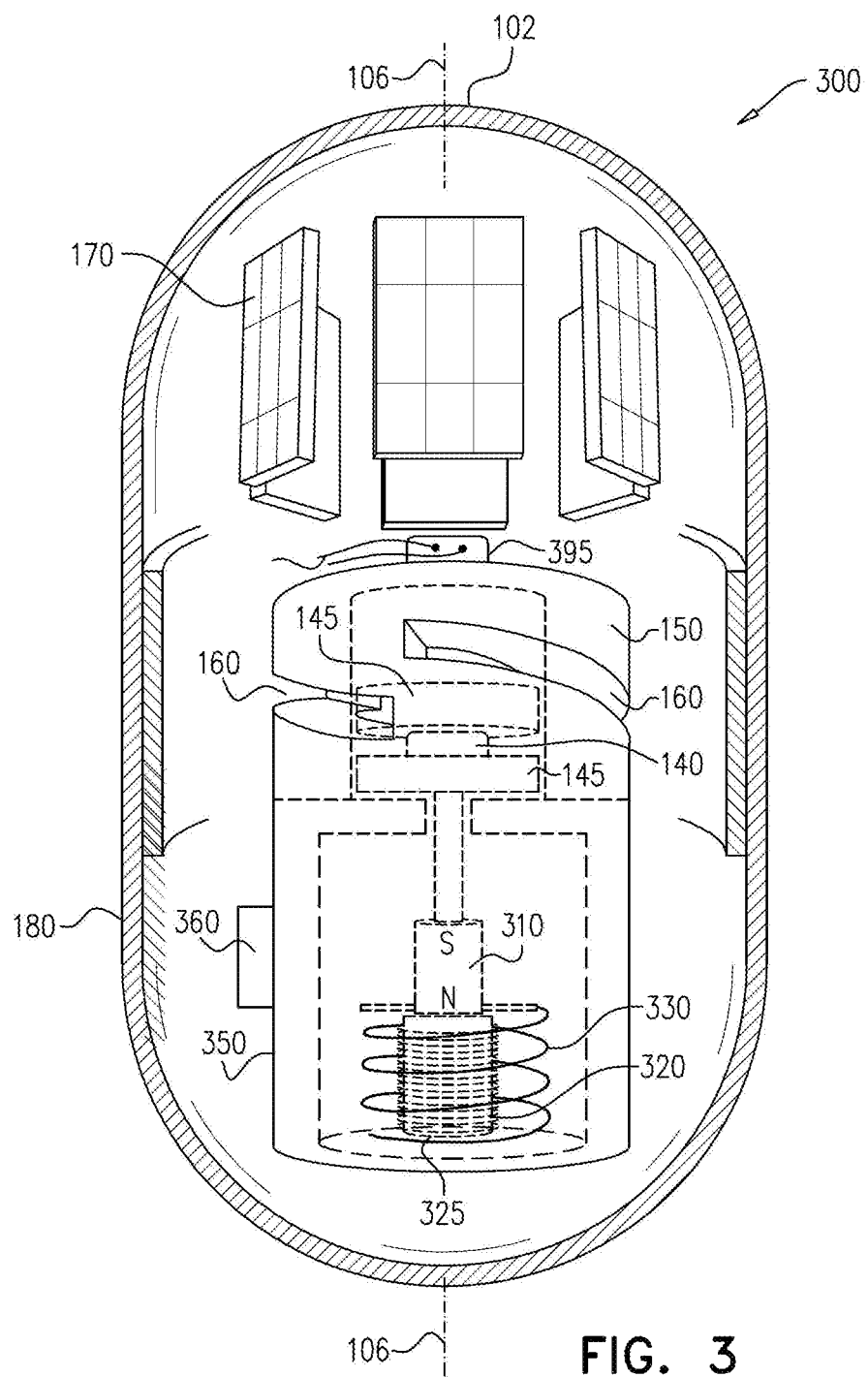
FIG. 3 is a schematic illustration of a cross sectional perspective view of an alternative failsafe imaging capsule blocking radiation, according to an exemplary embodiment of the disclosure.
Figure 4:
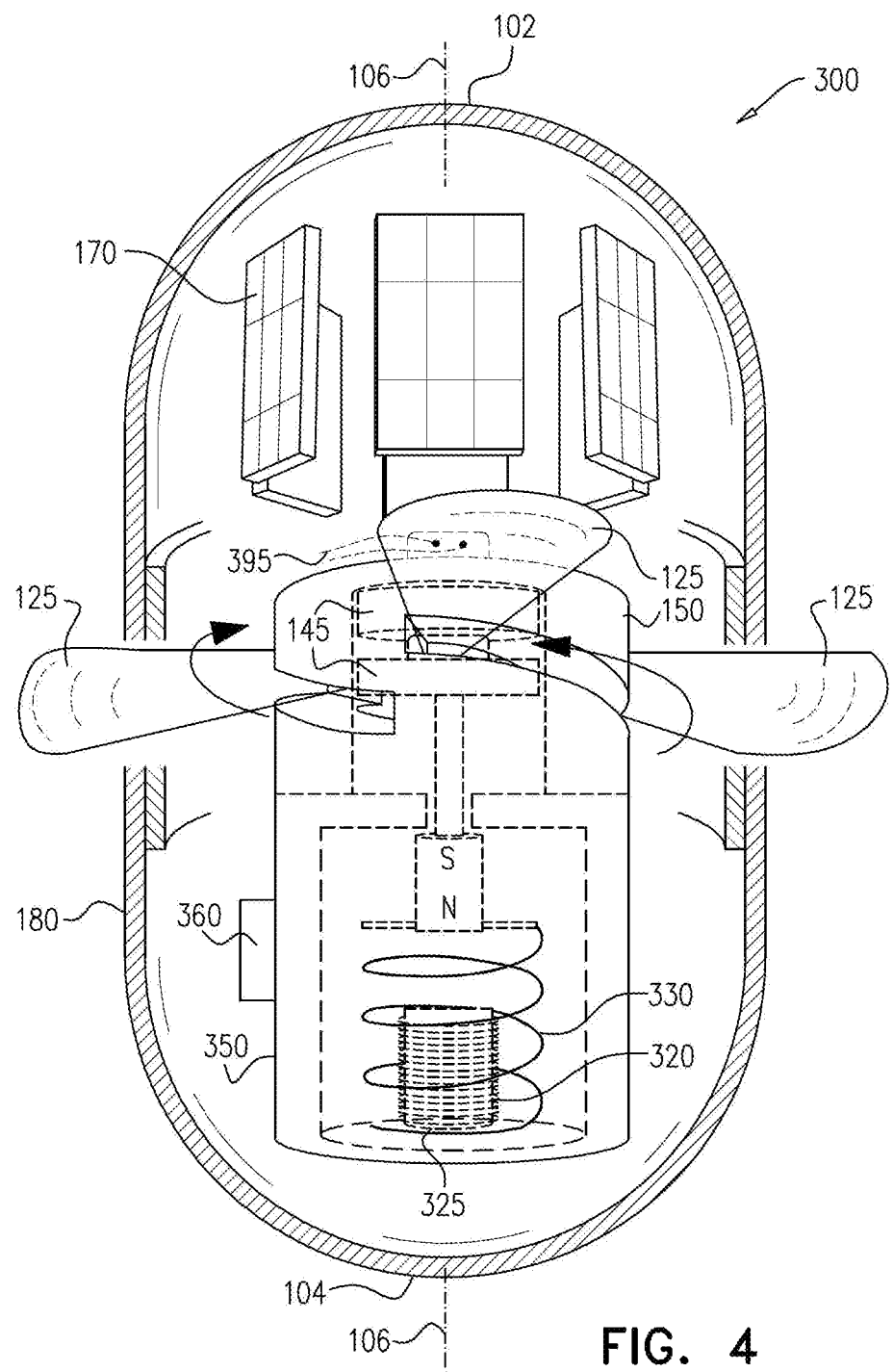
FIG. 4 is a schematic illustration of a cross sectional perspective view of an alternative failsafe imaging capsule emitting radiation, according to an exemplary embodiment of the disclosure.

FIG. 3 is a schematic illustration of a cross sectional perspective view of an alternative failsafe imaging capsule 300 blocking radiation and FIG. 4 is a schematic illustration of a cross sectional perspective view of an alternative failsafe imaging capsule 300 emitting radiation, according to an exemplary embodiment of the disclosure.

In an exemplary embodiment of the disclosure, imaging capsule 300 is similar to imaging capsule 100 however instead of using a linear voice coil motor to move radiation source 140, a solenoid 320 is wrapped around a ferromagnetic core 325 to form an electromagnet. Optionally, radiation source 140 is attached to a permanent magnet 310 that is attracted to ferromagnetic core 325, so that radiation source 140 is blocked by default by the lower part of collimator 150 (as shown in FIG. 3). In an exemplary embodiment of the disclosure, the solenoid 320 and ferromagnetic core 325 are located inside a housing 350 that is positioned below collimator 150. Alternatively, housing 350 may be part of collimator 150 that extends downward to enclose the solenoid 320 and ferromagnetic core 325.

In an exemplary embodiment of the disclosure, when current is applied to solenoid 320 a reverse magnetic field is established based on the direction of the current in the solenoid. Optionally, the permanent magnet 310 is repelled moving radiation source 140 from the first area to the second area of collimator 150 so that it emits radiation from the spiral slits 160 of collimator 150 and forms radiation beams 125. Optionally, spring 330 provides a returning force so that radiation source 140 can oscillate as described above for imaging capsule 100. The oscillatory frequency is dictated by the repulsion force, the spring constant, the mass of:

a) the magnet 310;
b) the radiation source 140;
c) the blocking disks 145; and
d) any other parts that move with them.

Optionally, these values may be selected to minimize power consumption while the radiation source 140 moves back and forth and emits radiation, causing rotation of the emitted radiation beams 125 back and forth around capsule 300.

In some embodiments of the disclosure, the position of the permanent magnet 310 can be monitored using a Hall Effect sensor 360 that varies its electrical output in response to a magnetic field. Alternatively or additionally, movement of the radiation source 140 is monitored by measuring the induced electromagnetic field in the solenoid 320 caused by the movement of the permanent magnet 310. Optionally, other alternative methods for measuring the position of the radiation source 140 may be employed, such as an optical sensor or an LVDT sensor to measure distance traveled etc. In some embodiments of the disclosure, the sensors mentioned above may be incorporated as part of a control loop to increase or decrease the driving current in order to position radiation source 140 and hence control the direction of the radiation beams to be positioned in a certain direction at a certain time.

One of the advantages of the current proposed linear actuator is the ability to stop the beam position at any location and immediate change direction of the scanning beam 125.

In an exemplary embodiment of the disclosure, a control 395 receives measurements from Hall Effect sensor 360 to determine the position of the permanent magnet 310. Optionally, current is provided to the solenoid 320 responsive to the determined position of the permanent magnet 310, so that the permanent magnet is pushed at the correct timing as it approaches the ferromagnetic core 325. In an exemplary embodiment of the disclosure, by providing electrical current to solenoid 320 at the correct time, energy consumption can be minimized mainly to compensate for friction and magnetic pull loss.

Figure 5:
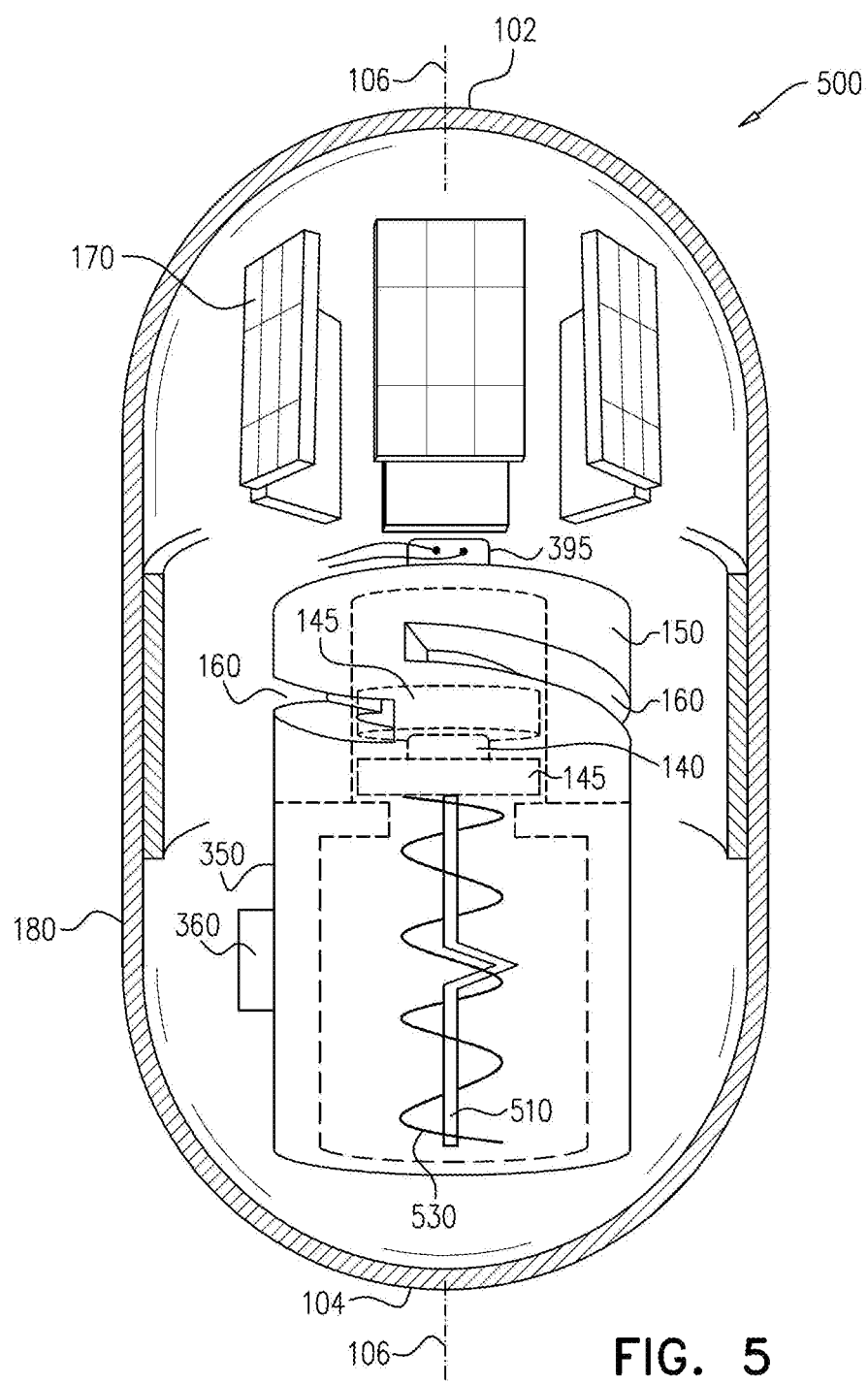
FIG. 5 is a schematic illustration of a cross sectional perspective view of an additional alternative failsafe imaging capsule blocking radiation, according to an exemplary embodiment of the disclosure.
Figure 6:
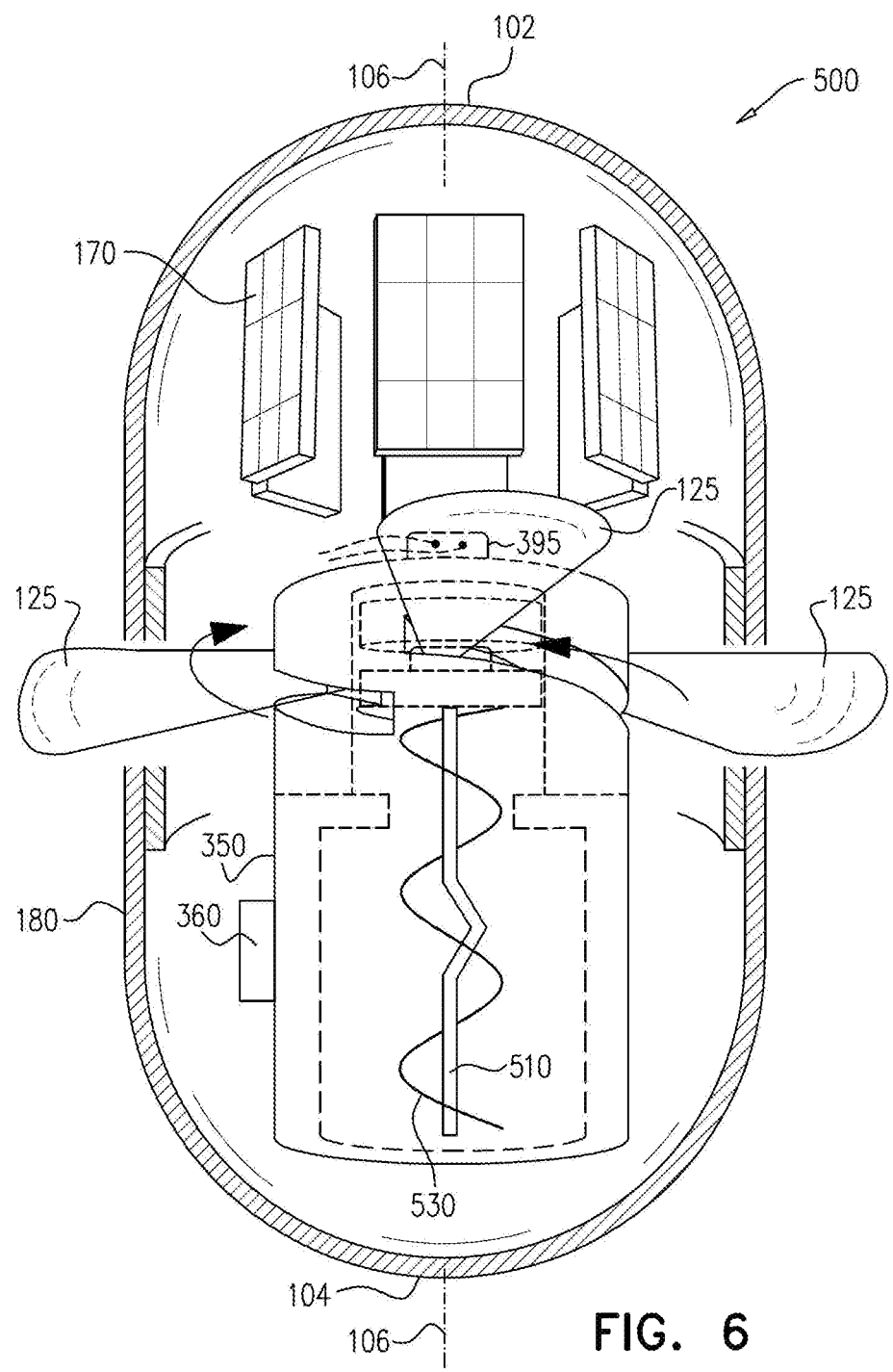
FIG. 6 is a schematic illustration of a cross sectional perspective view of an additional alternative failsafe imaging capsule emitting radiation, according to an exemplary embodiment of the disclosure.

FIG. 5 is a schematic illustration of a cross sectional perspective view of an additional alternative failsafe imaging capsule 500 blocking radiation and FIG. 6 is a schematic illustration of a cross sectional perspective view of an additional alternative failsafe imaging capsule 500 emitting radiation, according to an exemplary embodiment of the disclosure.

In an exemplary embodiment of the disclosure, imaging capsule 500 is similar to imaging capsule 300 however instead of using a solenoid 320 and permanent magnet 310 to move radiation source 140, imaging capsule 500 uses a shape memory alloy spring 510, for example from Nitinol or other type of expandable memory alloy provided in various shapes, which can expand responsive to the transfer of current through the material causing the material to heat and then retract to a remembered shape when no current is transferred, and the alloy cools down. Optionally, in one state (e.g. when no power is provided) the shape memory alloy spring 510 is retracted and radiation source 140 is blocked by collimator 150 and in a second state (e.g. when current is provided) shape memory alloy spring 510 expands moving radiation source 140 to the second area of collimator 150. In an exemplary embodiment of the disclosure, radiation source 140 emits radiation from spiral slit 160 during the transition from the first state to the second state. Optionally, by turning on and off the current the shape memory alloy spring 510 controls the emission of radiation. In some embodiments of the disclosure, a shaped memory polymer may be used.

In some embodiments of the disclosure, an additional spring 530 is connected to pull radiation source 140 back to the initial blocked position. Optionally, shape memory alloy spring 510 and spring 530 may be selected with the masses of the moving parts so that the radiation source will have a natural oscillation frequency matching the required imaging speed with a minimal amount of energy added to compensate for friction in the system.

In some embodiments of the disclosure, collimator 150 may have straight slits and be set to rotate (e.g. using a motor) to control the direction of radiation beam 125 when radiation source 140 is moved to the second area of collimator 150 to emit radiation.

FIG. 7 is a flow diagram of a method 700 of blocking and unblocking the emission of radiation with a linear actuator, according to an exemplary embodiment of the disclosure.

In an exemplary embodiment of the disclosure, collimator 150 is installed (710) inside an imaging capsule (e.g. 100, 300 or 500). Collimator 150 is designed having a first area that blocks radiation and a second area that emits radiation. Optionally, the second area has a spiral slit 160 so that the radiation is emitted in a different direction at each position along the elongated axis 106 through collimator 150. Alternatively, the collimator has a slit for emitting radiation in a specific direction and the collimator is rotated to emit radiation in different directions.

In an exemplary embodiment of the disclosure, radiation source 140 is positioned (720) at the first area of collimator 150 so that the radiation is initially blocked. Optionally, a mechanism is deployed (730) next to radiation source 150 and coupled to it. In an exemplary embodiment of the disclosure, the mechanism moves the radiation source 140 to the second area when power is provided to the mechanism and returns the radiation source 140 to be blocked in the first area when power is not available.

In some embodiments of the disclosure, the mechanism includes a linear voice coil motor to move the radiation source. Alternatively, the mechanism includes a permanent magnet and an electromagnet to move the radiation source 140. Further alternatively, the mechanism includes a shape memory alloy to move the radiation source 140. In some embodiments of the disclosure, other mechanisms can be used to control the position of the radiation source 140 in collimator 150.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure.

It will be appreciated by persons skilled in the art that the present invention is not limited to what has been particularly shown and described hereinabove. Rather the scope of the present invention is defined only by the claims, which follow.

We claim:

1. A fail safe concealment mechanism for a radiation imaging capsule, comprising:
    a collimator having a first area that blocks radiation and a second area that releases radiation, wherein the area that releases radiation in the collimator has a spiral slit that releases radiation in different directions as a function of the position of the radiation source inside the collimator;
    a radiation source that is initially positioned inside the collimator in the area that blocks radiation;
    a linear mechanism that moves the radiation source inside the collimator to the area that releases radiation when power is provided to the mechanism and automatically returns the radiation source to the area that blocks radiation when power is not provided to the mechanism.

2. A mechanism as in claim 1, further comprising a control unit that controls the timing of the linear mechanism.

3. A mechanism as in claim 2, wherein said control unit is programmed to provide power so that the motion frequency of the radiation source matches the natural resonance oscillatory frequency of the linear mechanism.

4. A mechanism as in claim 1, wherein as lire radiation source moves' linearly through the area that releases radiation In the collimator it emits a beam that scans 360° around the imaging capsule.

5. A mechanism as in claim 1, wherein said linear mechanism comprises a linear voice coil motor having a magnetic housing and a voice coil that is configured to move linearly back and forth.

6. A mechanism as in claim 1, wherein said linear mechanism comprises a spring to return the radiation source to the area that blocks radiation when power is not provided to the mechanism.

7. A mechanism as in claim 1, wherein said linear mechanism comprises a permanent magnet attached to the radiation source and a solenoid wrapped around a ferromagnetic core to form an electromagnet to selectively repel the radiation source to the area that releases radiation.

8. A mechanism as in claim 7, wherein said linear mechanism comprises a Hall Effect sensor or LDVT sensor to determine the position of the permanent magnet and enable a controller to control the motion of the radiation source in the collimator.

9. A mechanism as in claim 1, wherein said linear mechanism comprises a shape memory alloy spring that expands responsive to the transfer of electrical current through the material and retracts to a remembered shape when electrical current is not provided.

10. A method of equipping a radiation imaging capsule with, a fail safe concealment mechanism, comprising:
installing a collimator having a first area that blocks radiation and a second area that releases radiation, wherein the area that releases radiation in the collimator has a spiral slit that releases radiation in different directions as a function of the position of the radiation source inside the collimator;
positioning a radiation source inside the collimator in the area that blocks radiation;
deploying a linear mechanism that moves the radiation source inside the collimator to the area that releases radiation when power is provided to the mechanism and automatically returns the radiation source to the area that blocks radiation when power is not provided to the mechanism.

11. A method as in claim 10, wherein a control unit controls the timing of the linear mechanism.

12. A method as in claim 11, wherein said control unit is programmed to provide power so that the motion frequency of the radiation source matches the natural resonance oscillatory frequency of the linear mechanism.

13. A method as in claim 10, wherein as the radiation source moves linearly through the area that releases radiation in the collimator it emits a beam that scans 360° around the imaging capsule.

14. A method as in claim 10, wherein said linear mechanism comprises a linear voice coil motor having a magnetic housing and a voice coil that is configured to move linearly back and forth.

15. A method as in claim 10, wherein said linear mechanism comprises a spring to return the radiation source to the area that blocks radiation when power is not provided to the mechanism.

16. A method as in claim 10, wherein said linear mechanism comprises a permanent magnet attached to the radiation source and a solenoid wrapped around a ferromagnetic core to form an electromagnet to selectively repel the radiation source to the area that releases radiation.

17. A method as in claim 10, wherein said linear mechanism comprises a Hall Effect sensor or LDVT sensor to determine the position of the permanent magnet and enable a controller to control the motion of the radiation source in the collimator.

18. A method as in claim 10, wherein said linear mechanism comprises a shape memory alloy spring that expands responsive to the transfer of electrical current through the material and retracts to a remembered shape when electrical current is not provided.

* * * * *